US006825312B2

(12) United States Patent
Meyer et al.

(10) Patent No.: US 6,825,312 B2
(45) Date of Patent: Nov. 30, 2004

(54) POLYCARBONATES, POLYESTER CARBONATES AND POLYESTERS WITH SPECIAL BRANCHED TERMINAL GROUPS

(75) Inventors: Alexander Meyer, Krefeld (DE); Melanie Moethrath, Düsseldorf (DE); Werner Heuer Helmut, Krefeld (DE); Rolf Wehrmann, Krefeld (DE); Friedrich-Karl Bruder, Krefeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/420,670

(22) Filed: Apr. 22, 2003

(65) Prior Publication Data

US 2004/0030090 A1 Feb. 12, 2004

(30) Foreign Application Priority Data

Apr. 30, 2002 (DE) .......................................... 102 19 229

(51) Int. Cl.$^7$ .............................................. C08G 63/02
(52) U.S. Cl. .................... 528/272; 264/176.1; 264/219; 528/196; 528/271
(58) Field of Search .............................. 264/176.1, 219; 528/196, 271, 272

(56) References Cited

U.S. PATENT DOCUMENTS

| 3,166,606 | A | 1/1965 | Reinking et al. ............ 260/860 |
| 3,173,891 | A | 3/1965 | Fry et al. ....................... 260/47 |
| 4,153,780 | A | 5/1979 | Narita et al. ................. 528/198 |
| 4,230,548 | A | 10/1980 | Adelmann et al. ..... 204/159.14 |
| 4,330,663 | A | 5/1982 | Rosenquist .................. 528/176 |
| 5,043,403 | A | 8/1991 | Dujardin et al. ............. 525/462 |
| 5,783,653 | A | 7/1998 | Okamoto ..................... 528/196 |
| 5,959,065 | A | 9/1999 | Heuschen et al. ........... 528/198 |
| 6,140,457 | A | 10/2000 | LeGrand et al. ............. 528/196 |
| 6,258,922 | B1 | 7/2001 | Okamoto et al. ........... 528/196 |
| 2003/0096941 | A1 * | 5/2003 | Heuer et al. ................. 528/196 |

FOREIGN PATENT DOCUMENTS

| JP | 57-133149 | 8/1982 |
| JP | 6-256499 | 9/1994 |
| WO | 98/22522 | 5/1998 |
| WO | 01/05866 | 1/2001 |

OTHER PUBLICATIONS

Kunststoff–Handbuch, vol. VIII, pp. 149–151, Carl–Hanser–Verlag, Munich, (month unavailable) 1973, "Verarbeitung durch Schmelzen".

Kunstsoff–Handbuch 3, L. Bottenbruch, Hanser, München, (month unavailable) 1992, pp. 127–128, "Polycarbonate Polyacetale Polyester Celluloseester".

* cited by examiner

Primary Examiner—Terressa Boykin
(74) Attorney, Agent, or Firm—Joseph C. Gil; Aron Preis

(57) ABSTRACT

A phenolic compound having a branched structure is disclosed. The compound conforms to

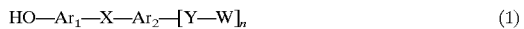

$$\text{HO—Ar}_1\text{—X—Ar}_2\text{—[Y—W]}_n \quad (1)$$

wherein $Ar_1$ and $Ar_2$ independently denote an optionally substituted mononuclear or polynuclear aromatic moiety, X and Y independently denote a single bond or a divalent radical, W denotes an optionally substituted mononuclear or polynuclear aromatic moiety or an aliphatic or cycloaliphatic radical, and
n is 1 to 5, is useful as a terminal group in polycarbonates, polyester carbonates and polyesters. Also disclosed is a process for producing such resins where the disclosed compound is a chain terminator.

10 Claims, No Drawings

POLYCARBONATES, POLYESTER CARBONATES AND POLYESTERS WITH SPECIAL BRANCHED TERMINAL GROUPS

FIELD OF THE INVENTION

The present invention relates to thermoplastic molding compositions and more particularly to compositions that contain any of polycarbonates, polyester carbonates and polyesters that are chain terminated with a phenolic compounds having a branched structure.

SUMMARY OF THE INVENTION

A phenolic compound having a branched structure is disclosed. The compound conforms to $$HO-Ar_1-X-Ar_2-[Y-W]_n \qquad (1)$$

wherein $Ar_1$ and $Ar_2$ independently denote an optionally substituted mononuclear or polynuclear aromatic moiety, X and Y independently denote a single bond or a divalent radical, W denotes an optionally substituted mononuclear or polynuclear aromatic moiety or an aliphatic or cycloaliphatic radical, and
n is 1 to 5, is useful as a terminal group in polycarbonates, polyester carbonates and polyesters. Also disclosed is a process for producing such resins where the disclosed compound is a chain terminator.

BACKGROUND OF THE INVENTION

Monofunctional terminal groups based on phenol, such as for example phenol, 4-alkylphenols and 4-cumylphenol, are frequently used for the production of polycarbonates (Kunststoff-Handbuch 3; L. Bottenbruch, Hanser, München 1992, p. 127; EP-A 0 353 594).

It is not known whether these conventionally used terminal groups have a positive effect on the flow behavior and/or the zero shear viscosity and/or the thermal stability and thus whether they have a positive effect on the processing properties of the corresponding polycarbonates.

The production of polycarbonates containing branched terminal groups is in principle known and is described for example in EP-A 0 794 209 and JP-A 06 256 499.

For example p-phenylphenol is known from U.S. Pat. Nos. 3,166,606 and 3,173,891 as a chain terminator for polycarbonates. From U.S. Pat. No. 4,330,663 polyester carbonates are known in which 4-butylbenzoyl chloride is used as chain terminator.

WO-A 00/50488 describes the use of di-tert.-alkylphenol as chain terminator.

From Japanese Offenlegungsschrift 57 13 31 49 polycarbonates are known that are modified with phenylpropylphenol, alkylphenols or naphthol as terminal groups.

Tritylphenol, cumylphenol, phenoxyphenol and pentadecylphenol are described in WO-A 01/05 866 as chain terminators for polycarbonates.

From EP-A 1 048 684 and WO-A 99/36 458 polycarbonates are known that have been modified for example with 4-(1,1,3,3-tetramethylbutyl)phenol and further branched alkyl phenols.

From JP-A 06 25 64 99 polycarbonates are known containing terminal groups of the structures

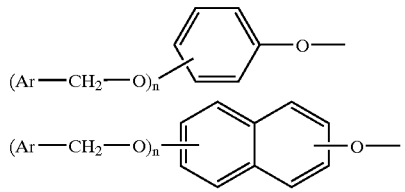

According to DE-A 38 03 939, chain terminators of the formula

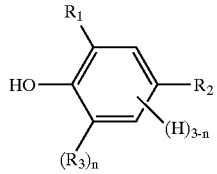

are used, wherein $R_1$, $R_2$, $R_3$ are identical or different and denote $C_2$–$C_{12}$-alkyl or $C_8$–$C_{20}$-aralkyl, at least one of the radicals $R_1$ or $R_2$ being a $C_8$–$C_{20}$-aralkyl radical, and wherein n has a value between 0.5 and 1.

WO-A 98/22522 describes branched phenols, their use as terminal groups in polycarbonates, and polycarbonates containing such terminal groups. Furthermore, an effect of these terminal groups in the polycarbonate is said to be a lower glass transition temperature. However, no details are given either of branched phenols of the aforedescribed type or of the effect of branched terminal groups on the zero shear viscosity and thermal stability of polycarbonates.

The polyester carbonates and polyesters with known terminal groups have the disadvantage however of relatively high zero shear viscosity and/or may tend to exhibit a reduction in molecular weight and/or material discolouration under thermal stress. Thus, polycarbonates that contain secondary or tertiary hydrogen atoms, above all in the benzyl position, may be degraded under thermal stress, such as for example in an extrusion process, as a result of which the corresponding material may be discoloured. Polycarbonates that contain ester groupings as terminal groups tend under thermal stress to undergo transesterification reactions and are therefore not suitable for the melt transesterification process. (Kunststoff-Handbuch Vol. VIII, p. 150, Carl-Hanser-Verlag, Munich 1973).

DETAILED DESCRIPTION OF THE INVENTION

Against the background of the prior art the object therefore exists of providing polycarbonates, polyester carbonates and polyesters—these are referred to herein below as poly(ester)(carbonate)- and/or suitable phenolic compounds as terminal groups, that do not exhibit the disadvantage of a high zero shear viscosity and at the same time do not undergo degradation under thermal stress, such as for example in an extrusion process or in injection moulding, and that may also be used in the melt transesterification process.

It has now surprisingly been found that this object is achieved by the use of terminal groups having a special branched, in particular dendrimer-like structure. These terminal groups positively influence the zero shear viscosity, i.e. the corresponding polycarbonate with a comparable molecular weight distribution exhibits a lower Zero shear viscosity and can therefore be processed more readily. In particular these special terminal groups have the advantage that they are also stable at high temperatures.

Phenolic terminal groups for polycarbonates having a dendrimer-like structure based on carbonyl-bridged or ether-bridged aryl systems have not hitherto been known.

The present invention accordingly provides polycarbonates, polyester carbonates and polyesters that contain branched, in particular dendrimer-like terminal groups based on aryl-CO- and/or aryl-O-couplings, the use of such polycarbonates, and special phenolic terminal groups suitable for use in the polycarbonates according to the invention, and/or the phenolic compounds on which the terminal groups are based.

The present invention accordingly also provides for the use of the phenolic compounds according to formula (1) for the production of terminal group-modified polymers and the phenolic compounds of the formula (2), as well as their preparation.

The phenolic compounds of the formula (1) are defined as follows:

$$HO-Ar_1-X-Ar_2-[Y-W]_n \quad (1)$$

wherein $Ar_1$ denotes an optionally substituted mononuclear or polynuclear aromatic parent group, X denotes a single bond or a divalent radical such as —O— or —CO—, $Ar_2$ denotes an optionally substituted mononuclear or polynuclear aromatic parent group, Y denotes a single bond or a divalent radical such as —O— or —CO—, W denotes an optionally substituted mononuclear or polynuclear aromatic parent group or an aliphatic or cycloaliphatic radical, and n is a variable between 1 and 5.

Preferred are phenolic compounds of the formula (1) that correspond more specifically to the formulae (2) and (3):

Compounds of the formula (2)

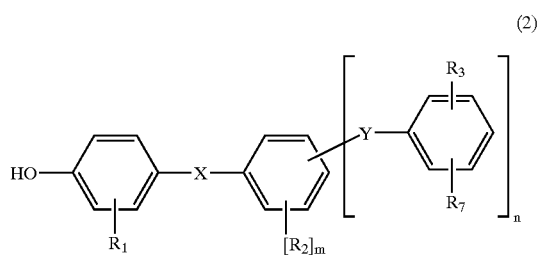

wherein $R_1$ denotes H, linear or branched $C_1$–$C_{18}$-alkyl, Cl or Br, preferably H or linear or branched $C_1$–$C_{12}$-alkyl, particularly preferably H or $C_1$–$C_8$-alkyl, and most particularly preferably H, X denotes a single bond or a divalent radical such as —O— or —CO—, $R_2$ denotes H, linear or branched $C_1$–$C_{18}$-alkyl, Cl or Br, preferably H or linear or branched $C_1$–$C_{12}$-alkyl, particularly preferably H or $C_1$–$C_8$-alkyl, and most particularly preferably all denote the same radical, especially H, Y denotes a single bond or a divalent radical such as —O— or —CO—, $R_3$, $R_7$ independent from each other denote H, linear or branched $C_1$–$C_{18}$-alkyl, cyclic $C_5$–$C_{18}$-alkyl, phenyl, phenyloxy, phenylcarboxy, benzyl, benzyloxy, naphthyl, naphthyloxy or naphthylcarboxy radicals, preferably $R_3$ equals $R_7$ equals H, linear or branched $C_1$–$C_{12}$-alkyl, cyclic $C_5$–$C_{12}$-alkyl, phenyl, phenyloxy, benzyloxy or naphthyloxy radicals, and particularly preferably H, linear or branched $C_1$–$C_{12}$-alkyl, cyclic $C_5$–$C_{12}$-alkyl, phenyl or phenyloxy radicals, very particularly preferred $R_3$ and $R_7$ denote the same group or residue.

m is a number between 0 and 3, n is a number between 2 and 5, wherein m and n must total ≦5. Particularly preferred is the combination in which m=0 and n=2.

Compounds of the formula (3)

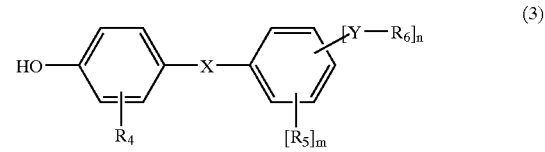

wherein

X and Y have the meanings given above, $R_4$ denotes H, linear or branched $C_1$–$C_{18}$-alkyl, Cl or Br, preferably H or linear or branched $C_1$–$C_{12}$-alkyl, particularly preferably H or $C_1$–$C_8$-alkyl, and most particularly preferably H, $R_5$ denotes H, linear or branched $C_1$–$C_{18}$-alkyl, Cl or Br, preferably H or linear or branched $C_1$–$C_{12}$-alkyl, particularly preferably H or $C_1$–$C_8$-alkyl, and most particularly preferably all denote the same radical, in particular H, $R_6$ denotes linear or branched $C_1$–$C_{18}$-alkyl, cyclic $C_5$–$C_{18}$-alkyl, and preferably linear or branched $C_1$–$C_{12}$-alkyl, cyclic $C_5$–$C_{12}$-alkyl, and particularly preferably all denote the same radical, in particular linear or branched $C_1$–$C_{12}$-alkyl, as well as cyclic $C_5$–$C_{12}$-alkyl radicals, and m is a number between 0 and 3, n is a number between 2 and 5, wherein m and n must total ≦5. Particularly preferred is the combination in which m=0 and n=2.

Most particularly preferred are in each case independently of one another the phenolic compounds that correspond to the formula 2a and 3a:

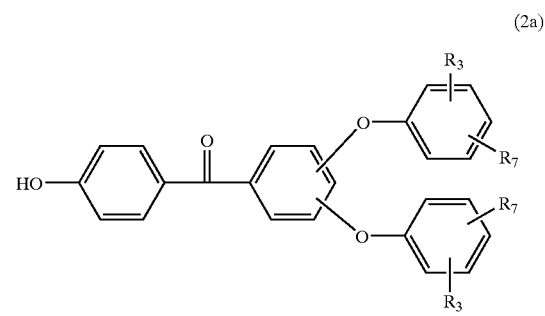

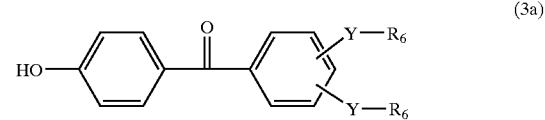

wherein in 2a and 3a the radicals $R_3$, $R_6$, $R_7$ and Y have the meanings given above.

Suitable terminal groups for the, modification of polycarbonates, polyester carbonates and polyesters are represented by formula (4):

$$-O-Ar_1-X-Ar_2-[Y-W]_n \quad (4)$$

wherein $Ar_1$, X, $Ar_2$, Y and W have the meanings given above.

Particularly suitable are the terminal groups of the formulae (4a) and (4b)

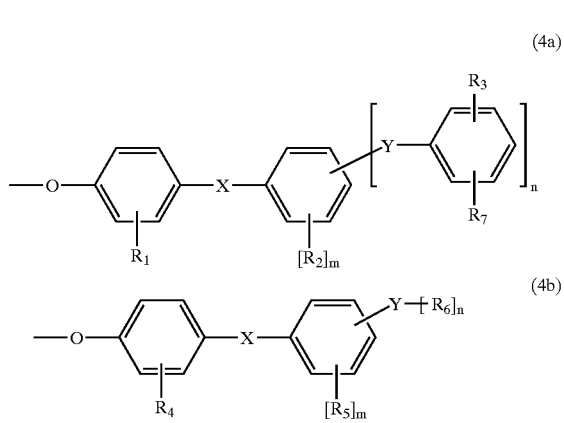

wherein the radicals X, Y, R₁ to R₇ and the variables n and m have the meanings given above.

Independently of one another there are most particularly preferred the terminal groups corresponding to the phenolic compounds of the formulae (2a) and (3a).

Preferred, particularly preferred, most particularly preferred or especially preferred, etc., are compounds that carry the substituents mentioned hereinbelow as preferred, particularly preferred, most particularly preferred or especially preferred, etc.

The radical definitions and explanations given above in general terms or as preferred ranges may however also be combined as desired with one another, i.e. between the respective ranges and preferred ranges. They apply as appropriate to the end products as well as to the precursors and intermediate products.

The present invention accordingly also provides thermoplastic polycarbonates, thermoplastic polyester carbonates and thermoplastic polyesters with terminal groups corresponding to the phenolic compounds of the formulae (1), (2) and (3).

Examples of phenolic compounds of the formula (1) are 3,5-diphenyloxy-4'-hydroxybenzophenone, 3,5-bis-(p-tert.-butylphenyloxy)-4'-hydroxybenzophenone, 3,5-bis-(p-n-butylphenyloxy)-4'-hydroxybenzophenone, 3,5-bis-(3,5-di-tert.-butylphenyl-oxy)-4'-hydroxybenzophenone, 3,5-bis-(p-iso-octylphenyloxy)-4'-hydroxybenzophenone, 3,5-dicyclooctyloxy-4'-hydroxybenzophenone, 3,5-dicyclododecyloxy-4'-hydroxybenzo-phenone, 3,5-bis-(benzoyl)-4'-hydroxybenzo-phenone and 3,5-di-tert.-butyl-4'-hydroxy-benzophenone.

The monophenols of the formulae (2) and (3) to be used according to the invention are not known in the literature. Branched fluorine-substituted hydroxyoligo(ether ketones) are known in the literature (C. J. Hawker, F. Chu, Macromolecules 1996, 29, 4370-4380). Multiply functional hydroxy compounds such as 1,3,5-tris-(2'-hydroxybenzoyl)-benzenes are also known (DE 19 59 399).

The production of the phenols of the formulae 2 and 3 may be carried out according to generally known processes. Thus, for example, phenols of the formulae 2 and 3 in which X and/or Y denote a carbonyl radical can in principle be produced by Friedel-Crafts reactions of optionally substituted aliphatic or aromatic carboxylic acid chlorides with optionally substituted aromatic compounds. Compounds of the formulae 2 and 3 in which X and/or Y denote a divalent radical such as —O— can in principle be produced by an Ullmann reaction of optionally substituted aromatic compounds with optionally substituted phenolates under the action of copper, at temperatures between 100° and 230° C. Alternatively these diaryl ethers can be produced by reacting optionally substituted arylboronic acids with phenolates. Compounds of the formulae 2 and 3 in which X and/or Y denote a single bond can be produced in a known manner by C—C coupling reactions. Thus, these may be obtained for example by an Ullmann reaction of halogen-substituted aromatic compounds. Preferably iodine-substituted, optionally higher substituted aromatic compounds, are reacted under the action of copper at temperatures between 100° and 300° C. In order to obtain the phenols of the formulae 2 and 3 according to the invention, it is necessary in the aforementioned reactions to introduce a protected phenolic OH group into the respective compound, from which the phenolic OH group can be released, preferably in the last stage of the synthesis. Such a protected phenolic OH group may for example be introduced into the respective compound in the aforedescribed reactions by means of an optionally substituted anisole derivative. In order to release the phenolic OH group the splitting of the methyl ether may be effected for example with BBr₃ in dichloromethane, with Me₃SiI in chloroform, or with aqueous HBr in acetic acid.

The production of the phenols of the general formula 2a may be carried out by methods known per se in the literature (see for example C. J. Hawker, F. Chu, Macromolecules 1996, 29, 4370–4380, A. Morikawa, K. Ono, Macromolecules 1999, 32, 1062–1068). Thus, dihalobenzoic acid can be converted by means of conventional acylating reagents such as for example oxalyl chloride or thionyl chloride into the corresponding acid chloride, and then reacted with optionally substituted, but in the p-position relative to the methoxy group unsubstituted, anisole derivatives under the addition of Lewis acids. Preferably difluorobenzoic acid can be converted with oxalyl or thionyl chloride into the corresponding acid chloride. This is reacted with optionally substituted, though in the p-position relative to the methoxy group unsubstituted, anisole derivatives, preferably under the action of for example FeCl₃, AlCl₃, BF₃, ZnCl₂, SnCl₄ or SbCl₅, in halogenated solvents such as for example CH₂Cl₂ or CHCl₃, at temperatures between −40° C. and 80° C. The optionally substituted dihalomethoxybenzo-phenone obtained in this way is reacted with optionally substituted phenols under the action of a base, optionally in combination with phase transfer reagents in polar aprotic solvents. Preferably the optionally substituted difluoromethoxy benzophenone is reacted with optionally substituted phenols in solvent mixtures such as: N,N-dimethylformamide/toluene, N,N-dimethylacetamide/toluene, dimethyl sulfoxide/toluene or N-methyl-pyrrolidone/toluene under the addition of for example alkali carbonates, alkali hydroxides or organic bases such as pyridine or diazabicycloundecene, optionally in combination with phase transfer reagents, at temperatures of 80° to 200° C. within 1 to 48 hours. Particularly preferably the optionally substituted difluoromethoxybenzophenone is reacted with optionally substituted phenols in solvent mixtures such as N,N-dimethylacetamide/toluene, dimethyl sulfoxide/toluene or N-methylpyrrolidone/toluene under the addition of K₂CO₃ or K₂CO₃/18-crown-6, at temperatures of 100° to 180° C. within 3 to 24 hours. In this connection the optionally substituted difluoromethoxybenzo-phenone is stirred under reflux with optionally substituted phenols as described above for 1 to 6 hours, following which the toluene/water mixture is removed with the aid of a water separator, and the solution is then stirred for a further 1 to 16 hours at temperatures between 130° and 180° C. The purification of the product is carried out preferably by column chromatography on silica gel (for example silica gel 60, 0.040–0.063 mm, Merck) using a mixture of n-hexane and ethyl acetate as eluent.

As an alternative to the conditions mentioned above, the previously produced phenolate can also be reacted directly with the dihalomethoxybenzophenone. In this case the addition of toluene and the base in the process described above is omitted.

In order to release the phenolic OH group the splitting of the methyl ether may be carried out for example with $BBr_3$ in dichloromethane, with $Me_3SiI$ in chloroform, or with aqueous HBr in acetic acid. This reaction is preferably carried out in a mixture of aqueous HBr solution and HBr solution in acetic acid.

Compounds of the formula 3a in which Y denotes for example a single bond can be produced in principle as follows: by Friedel-Crafts reaction of toluene with halogenated alkanes substituted aromatic compounds are obtained in a known manner, which are converted by subsequent oxidation of the methyl group on the aromatic compound, for example with potassium permanganate, into the correspondingly substituted benzoic acid. According to this method, 3,5-di-tert.-butylbenzoic acid for example can be produced in a known manner (see DE 32 21 818) by a Friedel-Crafts reaction of tert.-butyl chloride and toluene following by oxidation with potassium permanganate in aqueous pyridine. The substituted benzoic acid obtained in this way can be converted in a known manner with oxalyl chloride or thionyl chloride into the corresponding acid chloride. The acid chloride is reacted with optionally substituted, but in the p-position relative to the methoxy group unsubstituted, anisole derivatives, preferably under the action of for example $FeCl_3$, $AlCl_3$, $BF_3$, $ZnCl_2$, $SnCl_4$ or $SbCl_5$, in halogenated solvents such as for example $CH_2Cl_2$ or $CHCl_3$, at temperatures between −40° C. and 80° C. In order to release the phenolic OH group the splitting of the methyl ether may be carried out for example with $BBR_3$ in dichloromethane, with $Me_3SiI$ in chloroform, or with aqueous HBr in acetic acid. Preferably this reaction is carried out in a mixture of aqueous HBr solution and HBr solution in acetic acid.

Apart from the phenolic compounds of the formulae (1), (2) and (3) other phenols may also be co-used in amounts of up to 50 mole %, referred to the respective total amount of chain terminator, for the production of the polycarbonates, polyester carbonates and polyesters.

The present invention accordingly also provides for the use of the phenolic compounds of the formula (1), optionally in combination with other phenols, as chain terminators for the production of aromatic polycarbonates, aromatic polyester carbonates and aromatic polyesters, the other phenols being used in amounts of up to 50 mole %, preferably up to 25 mole %, referred to the respective total amount of chain terminators.

The present invention accordingly also provides thermoplastic polycarbonates, thermoplastic polyester carbonates and thermoplastic polyesters containing terminal groups derived from the phenolic compounds of the formulae (1), (2) and (3), illustrated by way of example but not exclusively by the polymers of the formula (5), (5)

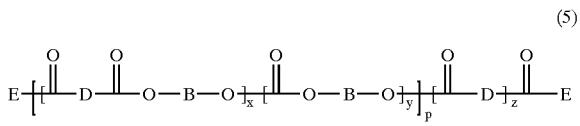

wherein (5)

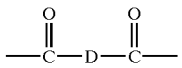

is the radical of an aromatic dicarboxylic acid, —O—B—O— is a bisphenolate radical AP@ is a whole number between 25 and 700, "x" and "y" are fractions from the range 0/p, 1/p, 2/p to p/p, where x+y=1, and "z"=0 or 1, and at least 50 mole % of the radicals E in (5) correspond to the phenolate radicals corresponding to the phenolic compounds of the formulae (1), (2) and (3) and at most 50 mole % of the radicals E in (5) correspond to a phenolate radical other than that corresponding to the phenolic compounds of the formulae (1), (2) or (3).

According to DE-A 2 119 799 the production of polycarbonates is carried out with the participation of phenolic terminal groups according to the phase boundary process as well as the homogeneous phase process.

For the production of polycarbonates by the phase interface process, reference may be made for example to H. Schnell, Chemistry and Physics of Polycarbonates, Polymer Reviews, Vol. 9, Interscience Publishers, New York 1964, pp. 33 ff. and to Polymer Reviews, Vol. 10, "Condensation Polymers by Interfacial and Solution Methods", Paul W. Morgan, Interscience Publishers, New York 1965, Chap. VIII, p. 325.

In addition it is also possible to produce the polycarbonates according to the invention from diary carbonates and diphenols according to the known polycarbonate process in the melt, the so-called melt transesterification process, which is described for example in WO-A 01/05866 and WO-A 01/05867. Transesterification processes (acetate process and phenyl ester process) are moreover described for example in U.S. Pat. Nos. 3,494,885, 4,386,186, 4,661,580, 4,680,371 and 4,680,372, in EP-A 26 120, 26 121, 26 684, 28 030, 39 845, 91 602, 97 970, 79 075, 14 68 87, 15 61 03, 23 49 13 and 24 03 01 as well as in DE-A 14 95 626 and 22 32 977.

Diaryl carbonates within the meaning of the present invention are those carbonic acid diesters of the formula (6)

(6)

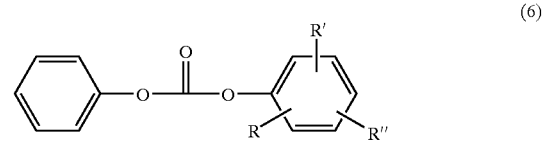

and formula (7), (7)

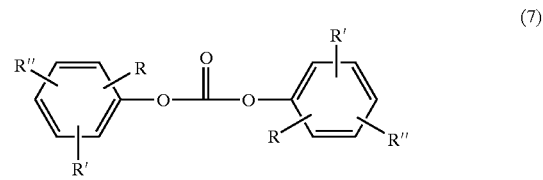

in which R, R' and R" may independently of one another denote H, optionally branched $C_1$–$C_{34}$-alkyl,/cycloalkyl, $C_7$–$C_{34}$-alkaryl or $C_6$–$C_{34}$-aryl or $C_6$–$C_{34}$-aryloxy, for example diphenyl carbonate, butylphenyl-phenyl carbonate, di-butylphenyl carbonate, isobutylphenyl-phenyl carbonate, di-isobutylphenyl carbonate, tert.-butylphenyl-phenyl carbonate, di-tert.-butylphenyl carbonate, n-pentylphenyl-phenyl carbonate, di-(n-pentylphenyl) carbonate, n-hexylphenyl-phenyl carbonate, di-(n-hexylphenyl) carbonate, cyclohexylphenyl-phenyl carbonate, di-cyclohexylphenyl carbonate, phenylphenol-phenyl carbonate, di-phenylphenol carbonate, isooctylphenyl-phenyl carbonate, di-isooctylphenyl carbonate, n-nonylphenyl-phenyl carbonate, di-(n-nonylphenyl) carbonate, cumylphenyl-phenyl carbonate, di-cumylphenyl carbonate, naphthylphenyl-phenyl carbonate, di-naphthylphenyl carbonate, di-tert.-butylphenyl-phenyl carbonate, di-(di-tert.-butylphenyl) carbonate, dicumylphenyl-phenyl carbonate, di-(dicumylphenyl) carbonate, 4-phenoxyphenyl-phenyl carbonate, di-(4-phenoxyphenyl) carbonate, 3-pentadecylphenyl-phenyl carbonate, di-(3-pentadecylphenyl) carbonate, tritylphenyl-phenyl carbonate, di-tritylphenyl carbonate, preferably diphenyl carbonate, tert.-butylphenyl-phenyl carbonate, di.-tert.-butylphenyl carbonate, phenylphenol-phenyl carbonate, di-phenylphenol carbonate, cumylphenyl-phenyl carbonate, di-cumylphenyl carbonate, particularly preferably diphenyl carbonate.

Diphenols for the polycarbonates according to the invention may for example be hydroquinone, resorcinol, dihydroxybiphenyls, bis-(hydroxyphenyl)-alkanes, bis-(hydroxyphenyl)-cycloalkanes, bis-(hydroxyphenyl)-sulfides, bis-(hydroxyphenyl)ethers, bis-(hydroxyphenyl)-ketones, bis-(hydroxyphenyl)-sulfones, bis-(hydroxy-phenyl)-sulfoxides, α,α'-bis-(hydroxyphenyl)-diisopropylbenzenes, as well as their nuclear-alkylated and nuclear-halogenated compounds, and also α,ω-bis-(hydroxyphenyl)-polysiloxanes.

Preferred diphenols are for example 4,4'-dihydroxybiphenyl (DOD), 2,2-bis-(4-hydroxyphenyl)-propane (bisphenol A), 1,1-bis-(4-hydroxyphenyl)-3,3,5-trimethylcyclohexane (bisphenol TMC), 1,1-bis-(4-hydroxyphenyl)-cyclohexane, 2,4-bis-(4-hydroxyphenyl)-2-methylbutane, 1,1-bis-(4-hydroxyphenyl)-1-phenylethane, 1,1-bis-(4-hydroxyphenyl)-p-diisopropylbenzene, 1,3-bis-[2-7(4-hydroxyphenyl)-2-propyl]-benzene (bisphenol M), 2,2-bis-(3-methyl-4-hydroxyphenyl)-propane, 2,2-bis-(3-chloro-4-hydroxyphenyl)-propane, bis-(3,5-dimethyl-4-hydroxyphenyl)-methane, 2,2-bis-(3,5-dimethyl-4-hydroxyphenyl)-propane, 2,2bis-(3, 5-dimethyl-4-hydroxyphenyl)-sulfone, 2.4-bis-(3,5-dimethyl-4-hydroxyphenyl)-2-methylbutane 2,2-bis-(3,5-dichloro-4-hydroxyphenyl)-propane and 2,2-bis-(3,5-dibromo-4-hydroxyphenyl)-propane.

Particularly preferred diphenols are for example 2,2-bis-(4-hydroxyphenyl)-propane (bisphenol A), 1,3-bis[2-(4-hydroxyphenyl)-2-propyl]-benzene (bisphenol M), 2,2-bis-(3,5-dimethyl-4-hydroxyphenyl)-propane, 1,1-bis-(4-hydroxyphenyl)-1-phenyl-ethane, 2,2-bis-(3,5-dichloro-4-hydroxyphenyl)-propane, 0.2,2-bis-(3,5-dibromo-4-hydroxyphenyl)-propane, 1,1-bis-(4-hydroxyphenyl)-cyclohexane and 1, 1-bis-(4-hydroxyphenyl)-3,3,5-trimethylcyclohexane (bisphenol TMC).

Most particularly preferred are 2,2-bis-(4-hydroxyphenyl)-propane (bisphenol A), 1,3-bis[2-(4-hydroxyphenyl)-2-propyl]benzene (bisphenol M) and 1,1-bis-(4-hydroxy-phenyl)-3,3,5-trimethylcyclohexane (bisphenol TMC).

The diphenols may be used alone or as a mixture with one another; homopolycarbonates as well as copolycarbonates are suitable. The diphenols are known in the literature or can be produced by processes known in the literature (see for example H. J. Buysch et al., Ullmann's Encyclopedia of Industrial Chemistry, VCH, New York 1991, 5$^{th}$ Ed., Vol. 19, p. 348).

There may also be used minor amounts, preferably amounts between 0.05 and 2.0 mole % referred to the moles of diphenols employed, of trifunctional or multifunctional compounds, in particular those with three or more than three phenolic hydroxy groups, as so-called branching agents. Deviations from the idealised formula (5), which is shown only by way of example, thereby obviously occur since branching structures are involved, in contrast to the specified structures D and B.

Some of the compounds that can be used containing three or more than three phenolic hydroxy groups are for example phloroglucinol, 4,6-dimethyl-2,4,6-tri-(4-hydroxyphenyl)-hept-2-ene, 4,6-dimethyl-2,4,6-tri-(4-hydroxyphenyl)-heptane, 1,3,5-tri-(4-hydroxyphenyl)-benzene, 1,1,1-tri-(4-hydroxyphenyl)-ethane, tri-(4-hydroxyphenyl)-phenylmethane, 2,2-bis-[4,4-bis-(4-hydroxyphenyl)-cyclohexyl]-propane, 2,4-bis-(4-hydroxyphenylisopropyl)-phenol, 2.6-bis-(2-hydroxy-5'-methylbenzyl)-4-methylphenol, 2-(4-hydroxyphenyl)-2-(3,4-dihydroxyphenyl)-propane, hexa-[4-(4-hydroxyphenylisopropyl)-phenyl]-orthoterephthalic acid ester, tetra-[4-(4-hydroxyphenylisopropyl)-phenoxy]-methane, tetra-(4-hydroxyphenyl)-methane and 1,4-bis-(4',4"-dihydroxy-triphenyl)-methylbenzene.

Further possible branching agents are 2,4-dihydroxybenzoic acid, trimesic acid, cyanuric chloride and 3,3-bis-(3-methyl-4-hydroxyphenyl)-2-oxo-2,3-dihydroindole.

The branching agents which are optionally co-used in an amount of 0.05 to 2 mole % referred to diphenols employed, may either be added together with the diphenols themselves and the molecular weight regulators according to the invention to the aqueous alkaline phase, or are added, dissolved in an organic solvent, before the phosgenation.

The aromatic polycarbonates of the present invention have weight average molecular weights $M_W$ (determined by gel permeation chromatography and calibration with a polystyrene standard) between 5000 and 200000, preferably between 10000 and 80000 and particularly preferably between 15000 and 40000.

The relative solution viscosities are correspondingly between 1.10 and 1.60 measured in methylene chloride (0.5 g of polycarbonate in 100 ml of methylene chloride at 23° C.).

Polyester carbonates according to the invention are those that are built up from at least one diphenol, from at least one aromatic dicarboxylic acid and from carbonic acid.

Suitable aromatic dicarboxylic acids are for-example orthophthalic acid, terephthalate acid, isophthalic acid, tert.-butylisophthalic acid, 3,3'-diphenyldicarboxylic acid, 4,4'-diphenyletherdicarboxylic acid, 4,4'-diphenylsulfonedicarboxylic acid, 3,4'-benzophenonedicarboxylic acid, 2,2-bis-(4-carboxyphenyl)-propane and trimethyl-3-phenyl-indane-4,5-dicarboxylic acid.

Of the aromatic dicarboxylic acids, terephthalic acid and/or isophthalic acid are particularly preferably used.

Suitable diphenols are those mentioned hereinbefore for the polycarbonate production. Carbonic acid may be incorporated either via phosgene or via diphenyl carbonate into the polyester carbonates, depending on the choice of production process, i.e. depending on whether phase interface polycondensation or melt transesterification is employed for the polyester carbonate production.

The same applies as regards the aromatic dicarboxylic acids; these are employed either as aromatic dicarboxylic acid dichlorides in the two-phase interface process or as dicarboxylic acid diesters in the melt transesterification process.

The production of the polyester carbonates according to the invention is carried out according to know production methods, i.e. as already mentioned, according to the phase interface process or according to the melt transesterification process for example.

The polyester polycarbonates according to the invention may be linear as well as branched in a known manner. The aromatic polyester carbonates of the present invention have mean weight-average molecular weights $M_W$ (determined by gel permeation chromatography with polystyrene calibration) preferably between 10000 and 250000.

The molar ratio of carbonate units to aromatic dicarboxylate units in the polyester carbonates according to the invention is preferably 95:5 to 5:95, more preferably between 90:10 to 10:90, particularly preferably between 80:20 and 20:80, and most particularly preferably between 60:40 and 40:60.

In the case of the polyesters (5) according to the invention "z" may be 0 as well as 1.

Aromatic polyesters according to the invention are those formed from at least one diphenol and at least one aromatic dicarboxylic acid.

Suitable diphenols and dicarboxylic acids are those mentioned hereinbefore for the polyester carbonate production.

The aromatic polyesters according to the invention are produced by known production processes (see for example Kunststoff-Handbuch, Vol. VIII, p. 695 ff, Carl-Hanser-Verlag Munich, 1973).

The aromatic polyesters according to the invention may be linear as well as branched in a known manner.

The aromatic polyesters according to the invention have mean weight-average molecular weights $M_W$ (determined by the light scattering method) preferably between 25000 and 70000; this corresponds to degrees of polymerisation Ap@ in formula (5) of about 80 to 270, where "x"=1, "y"=0 and "z"=1.

The amount of monophenols of the formulae (1), (2) or (3) according to the invention that are to be used for the production of the polycarbonates, polyester carbonates or polyesters according to the invention is between 0.5 mole % and 8 mole %, preferably between 2 mole % and 6 mole % referred to the diphenols used in each case.

Further suitable chain terminators are the customary monophenols, such as for example phenol, 4-alkylphenols and 4-cumylphenol.

The present invention accordingly also provides a process for the production of the polycarbonates, polyester carbonates or polyesters according to the invention from diphenols, monophenols, carbonic acid derivatives and/or dicarboxylic acid derivatives according to process conditions known per se, which process is characterised in that monophenols of the formulae (1), (2) or (3) are employed as chain terminators in amounts of 0.5 mole % to 8 mole %, preferably 2 mole % to 6 mole %, referred in each case to moles of diphenols, in which connection up to 50 mole %, preferably up to 25 mole %, referred in each case to the total amount of chain terminators, may be replaced by other monophenols.

In the case of the phase interface polycondensation process the chain terminators of the formulae (1), (2) or (3) may be added before, during or after the phosgenation in solution. The solvents suitable for dissolving the chain terminators of formulae (1), (2) or (3) are for example methylene chloride, chlorobenzene or acetonitrile, as well as mixtures of these solvents.

In the case of the melt transesterification process, in accordance with the process according to the invention it is possible to add the chain terminators of the formulae (1), (2) or (3) at any point in the reaction; in this connection the addition may be split into several portions.

The present invention also provides the polycarbonates, polyester carbonates and polyesters obtainable by the process according to the invention.

Diphenols for the production of the polycarbonates, polyester carbonates and polyesters according to the invention may also be polymers or condensates containing phenolic terminal groups, with the result that polycarbonates or polyester carbonates or polyesters with block structures may also be incorporated according to the invention.

The polycarbonates, polyester carbonates and polyesters according to the invention may be worked up in a known manner and processed into suitable moulded articles, for example by extrusion or injection moulding. Other aromatic polycarbonates and/or other aromatic polyester carbonates and/or other aromatic polyesters may also be mixed in a known manner with the polycarbonates, polyester carbonates and polyesters according to the invention.

There may also be added in the usual amounts to the polycarbonates, polyester carbonates and polyesters according to the invention additives that are conventionally used for these thermoplastics, such as fillers, UV stabilisers, thermal stabiliser, antistatics and pigments; the mould release behavior, the flow behavior and/or the flame resistance may also be improved if necessary by adding external mold release agents, flow improvers and/or flameproofing agents (for example alkyl and aryl phosphites, phosphates, phosphanes, low molecular weight carboxylic acid esters, halogenated compounds, salts, chalk, quartz flour, glass and carbon fibres, pigments and combinations thereof. Such compounds are described for example in WO 99/55772, pp. 15–25, and in "Plastics Additives", R. Gächter and H. M üller, Hanser Publishers 1983.

The polycarbonates, polyester carbonates and polyesters according to the invention, optionally mixed with other thermoplastics and/or conventional additives, may be processed into suitable molded articles/extrudates, and used in all cases where known polycarbonates, polyester carbonates and polyesters are already employed. On account of their property profile they are suitable in particular as substrate materials for optical data storage media such as for example CD, CD-R, DVD or DVD-R, but may also be used for example as films in the electrical sector, as molded parts in vehicle production, and as sheets for coverings in the safety sector.

Further possible applications of the polycarbonates according to the invention include:
1. Safety panels, which as is known are required in many areas of housings, vehicles and aircraft, as well as helmet shields.
2. Production of foils, especially ski foils.
3. Production of molded articles (see for example U.S. Pat. No. 2,964,794), for example 1- to 5-gallon water containers.
4. Production of light-permeable panels, in particular hollow-cavity panels, for example for covering buildings such as railways, greenhouses and lighting installations.
5. Production of optical data storage media.
6. Production of traffic light housings or vehicle number plates.
7. Production of foams (see for example DE-AS 1 031 507).
8. Production of fibres and threads (see for example DE-AS 1 137 167 and DE-OS 1 785 137).
9. As translucent plastics materials with a glass fibre content for light technology purposes (see for example DE-OS 1 554 020).

10. As translucent plastics materials containing barium sulfate, titanium dioxide and/or zirconium oxide and/or organic polymeric acrylate rubbers (EP-A 634 445, EP-A 269324) for the production of light-permeable and light-scattering molded parts.
11. Production of precision injection-molded small parts, such as for example lens mountings. For this purpose polycarbonates are used that contain glass fibres, which optionally may additionally contain about 1–10 wt. % of $MOS_2$, referred to the total weight.
12. Production of optical instrument parts, in particular lenses for photographic cameras and film cameras (see for example DE-OS 2 701 173).
13. As light-transmission carriers, in particular as light-conducting cables (see for example EP-A1 0 089 801).
14. As electrical insulation materials for electrical leads and for plug housings as well as plug-and-socket connectors.
15. Production of mobile telephone housings having improved resistance to perfume, shaving water and sweat.
16. Network interface devices.
17. As carrier material for organic photoconductors.
18. Production of lamps/lights, e.g. headlamps, scattered light panels or internal lenses.
19. For medical applications, e.g. oxygenators, dialysis equipment.
20. For foodstuff applications, e.g. bottles, utensils and chocolate molds.
21. For applications in the automobile sector where contact with fuels and lubricants may occur, such as for example bumpers, optionally in the form of suitable blends with ABS or suitable rubbers.
22. For sports articles, such as for example slalom poles or ski shoe fastenings.
23. For household articles, for example kitchen sink units and letter box housings.
24. For housings, for example electrical distribution cabinets.
25. Housings for electric toothbrushes and hairdryers.
26. Transparent washing machine Abullseyes@ with improved resistance to detergents.
27. Protective goggles optical correction glasses.
28. Lamp coverings for kitchen appliances with improved resistance to kitchen atmospheres, in particular oil vapours.
29. Packaging films for medicaments.
30. Chip boxes and chip carriers.
31. For other applications, such as for example stall-feeding doors or animal cages.

The molded articles and extrudates produced from the polymers according to the invention are also covered by this application.

The invention is further illustrated but is not intended to be limited by the following examples in which all parts and percentages are by weight unless otherwise specified.

EXAMPLES

Example 1
Preparation of Difluorobenzoic Acid Chloride 22.0 g (0.139 mole) of 3,5-difluorobenzoic acid are added under argon to a round-bottomed flask and 323.33 g (2.718 moles) of thionyl chloride are added dropwise while stirring. After the addition of a few drops of N,N-dimethylformamide the mixture is heated to 70° C. and is stirred until the end of the evolution of gas. The remaining thionyl chloride is then distilled off in a water jet vacuum. 21.19 g (86%) of a viscous oil are obtained.

$^1$H-NMR (400 MHz, $CDCl_3$) δ=7.69–7.62 (m, 2H), 7.19–7.12 (m, 1H).

Example 2
Preparation of 3,5-difluoro-4'-methoxybenzophenone 12.98 g (0.120 mole) of anisole are dissolved in 40 ml of dichloromethane under an argon atmosphere in a round-bottomed flask and cooled to 0° C.

16.0 g (0.120 mole) of aluminium chloride are added in small portions. The mixture is stirred for 10 minutes. A solution of 21.19 g (0.120 mole) of difluorobenzoic acid chloride (dissolved in 100 ml of dichloromethane) is added dropwise. The mixture is stirred for a further 4 hours at 0° C. and the solution is allowed to warm up to room temperature. 90 ml of hydrochloric acid solution (10%) are carefully added and the organic phase is separated from the aqueous phase. The aqueous phase is extracted with dichloromethane. The combined organic phases are washed with NaOH (1 mole/l) and then washed neutral, once with demineralised water and twice with saturated NaCl solution, dried over magnesium sulfate, filtered and concentrated by evaporation. The solid obtained in this way is recrystallised in n-hexane. After drying, white, needle-shaped crystals remain (19.25 g, 65%; m.p.: 90° C.).

$^1$H-NMR (400 MHz, $CDCl_3$) δ=7.81 (d, 2H), 7.28–7.24 (m, 2H), 7.05–6.96 (m 3,H), 3.90 (s, 3H).

Example 3
Preparation of 3,5-diphenyloxy-4'-methoxybenzophenone 19.0 g (0.077 mole) of 3,5-difluoro-4'-methoxybenzophenone are dissolved under argon in a mixture of 200 ml of dimethyl sulfoxide and 200 ml of toluene. 28.56 g (0.207 mole) of finely powdered potassium carbonate are added to this solution. The solution is stirred under reflux for 4 hours, the water formed being removed in a water separator. The toluene is then completely distilled off and the reaction mixture is stirred for a further 3 hours at 150° C. A further 28.56 g (0.207 mole) of finely powdered potassium carbonate and 50 ml of toluene are added. The mixture is heated under reflux and the toluene is distilled off. The solution is stirred for a further 4 hours at 150° C. After cooling, the solution is poured onto ice. The solution is neutralised by adding HCl solution (10%). Extraction with diethyl ether is performed several times. The combined organic phases are washed with saturated sodium chloride solution. The product is dried over magnesium, sulfate and the solvent is removed in vacuo. The crude product is chromatographed on silica gel (silica gel 60, 0.040–0.063 mm, Merck) using n-hexane/ethyl acetate (19:1). 14.90 g (49%) of a pale yellow oil are obtained.

$^1$H-NMR (400 MHz, $CDCl_3$) δ=7.84–7.78 (m, 2H), 7.39–7.30 (m, 4H), 7.15–7.09 (m, 2H), 7.08–7.02 (m, 6H), 6.95–6.90 (m, 2H), 6.86 (t, 1H), 3.86 (s, 3H).

HPLC-MS (ES), m/z: 396[M$^+$].

Example 4
Preparation of 3,5-diphenyloxy-4'-hydroxybenzophenone 14.90 g (0.038 mole) of 3,5-diphenyloxy-4'-methoxybenzophenone are dissolved under argon in a mixture of 60 ml of hydrobromic acid (48% in water) and 120 ml of hydrobromic acid (33% solution in acetic acid). The mixture is stirred for 4 hours under reflux. A further 100 ml of hydrobromic acid (330/solution in acetic acid) and 50 ml of hydrobromic acid (48% in water) are added to the reaction solution. The reaction mixture is stirred for a further 6 hours under reflux. The reaction mixture is then poured onto ice and extracted several times with diethyl ether. The organic phases are combined and extracted several times with NaOH solution (20%). The aqueous phases are combined and washed neutral with HCl solution. The neutralised aqueous phase is then extracted several times with diethyl ether. The organic phases are combined, dried over magnesium sulfate, and the solvent is removed in vacuo. The crude product is taken up in a small amount of diethyl ether and filtered over silica gel. After removing the solvent and drying the residue in a high vacuum, 11.25 g (78%) of a white solid are obtained.

$^1$H-NMR (400 MHz, CDCl$_3$) δ=7.79–7.74 (m, 2H), 7.38–7.31 (m, 4H), 7.16–7.10 (m, 2H), 7.08–7.02 (m, 6H), 6.89–6.83 (m, 3H), 5.35 (s, 1H).

Example 5

Preparation of 3,5-bis-(3,5-di-tert.-butylphenyloxy)-4'-methoxybenzophenone 1.35 g (5.4 mmoles) of 3,5-difluoro-4'-methoxybenzophenone are dissolved in a mixture of 80 ml of dimethyl sulfoxide and 80 ml of toluene under an argon atmosphere. 2.03 g (14.7 mmoles) of finely powdered potassium carbonate are added to this solution. 4.49 g (21.8 mmoles) of 3,5-di-tert.-butylphenol and 0.575 g (2.2 mmoles) of hexaoxacyclo-octadecane (18-crown-6) are added while stirring. The mixture is stirred under reflux for 4 hours and the water formed during the reaction is removed in a water separator. A further 0.575 g (2.2 mmoles) of hexaoxacyclo-octadecane (18-crown-6) and 0.98 g (7.1 mmoles) of finely powdered potassium carbonate are added to the reaction mixture. The mixture is stirred for a further 6 hours at 150° C. The mixture is allowed to cool and the solution is poured onto ice. The solution is neutralised by adding HCl solution (10%). Extraction with diethyl ether is performed several times. The combined organic phases are then washed with saturated sodium chloride solution. The organic phase is dried over magnesium sulfate and the solvent is removed in vacuo. The crude product is chromatographed on silica gel (silica gel 60, 0.040–0.063 mm, Merck) using a mixture of n-hexane and ethyl acetate (19:1) as eluent. 2.00 g (59%) of a pale yellow solid are obtained.

$^1$H-NMR (400 MHz, CDCl$_3$) δ=7.85–7.80 (m, 2H), 7.19–7.16 (m, 2H), 7.05–7.01 (m, 2H), 6.94–6.88 (m, 6H), 6.81–6.78 (m, 1H), 3.86 (s, 3H), 1.28 (s, 36).

MALDI-TOF: 621 [M+H$^+$], 627 [M+Li$^+$].

Example 6

Preparation of 3,5-bis-(3,5-di-tert.-butylphenyloxy)-4'-hydroxybenzo-phenone 2.80 g (4.5 mmoles) of 3,5-bis-(3,5-di-tert.-butylphenyloxy)4'-methoxybenzo-phenone are dissolved under argon in 100 ml of hydrobromic acid solution (33% in acetic acid). 0.23 g (0.5 mmole) of: hexadecyltributylphosphonium bromide is added thereto. The solution is stirred for 3 hours at 50° C. The course of the reaction is followed by thin layer chromatography. An additional 100 ml of hydrobromic acid (33% in glacial acetic acid) and 20 ml of aqueous hydrobromic acid (48%) are added to the reaction solution. The solution is stirred for a further 18 hours under reflux. After cooling the solution, the reaction mixture is poured onto ice and extracted several times with diethyl ether. The combined organic phases are washed with saturated NaCl solution. The product is dried over magnesium sulfate and the solvent is removed in vacuo. The crude product is chromatographed on silica gel (silica gel 60, 0.040–0.063 mm, Merck) using a mixture of n-hexane/ethyl acetate (9:1). After removing the solvent and drying the residue in a high vacuum, 2.47 g (90%) of a white solid are obtained.

$^1$H-NMR (400 MHz, CDCl$_3$) δ=7.79–7.77 (m, 2H), 7.18 (s, 2H), 7.03 (s, 2H), 6.89 (s, 4H), 6.87–6.85 (m, 2H), 6.79 (s, 1H), 1.28 (s, 36H).

Example 7

Preparation of 3,5-di-tert.-butyl-4'-methoxybenzophenone 5.00 g (0.021 mole) of di-tert.-butylbenzoic acid are added under argon to a reaction vessel; 49.69 g (0.418 mole) of thionyl chloride are added dropwise while stirring. 0.05 ml of N,N-dimethylformamide is also added to the reaction solution. The mixture is heated while stirring to 70° C. and stirring is continued until the formation of gas has finished. The excess thionyl chloride is then distilled off. 5.39 g of a colourless viscous oil remains, which is used without further working-up.

2.25 g (0.021 mole) of anisole are dissolved in 30 ml of methylene chloride in a round-bottomed flask and cooled to 0° C. 2.78 g (0.021 mole) of aluminium chloride are added in small portions to this solution and the mixture is then stirred for 10 minutes. The acid chloride (colourless oil, see above) is dissolved in 50 ml of methylene chloride and added dropwise at 0° C. to the solution of anisole/AlCl$_3$. After all the acid chloride has been added the reaction mixture is stirred for a further 75 minutes at 0° C. The solution is then heated to room temperature.22 ml of HCl solution (10%) are carefully added dropwise to the reaction mixture. The phases are separated in a separating funnel. The aqueous phase is extracted with methylene chloride and the organic phases are combined. These are washed with distilled water and finally with saturated NaCl solution. The product is dried over magnesium sulfate and the solvent is removed in vacuo. After drying in a high vacuum, 6.38 g (94%) of product are obtained in the form of a pale yellow solid.

$^1$H-NMR (400 MHz, CDCl$_3$) δ-7.85 (d, 2H), 7.62 (s, 1H), 7.59 (s, 2H), 6.97 (d, 2H), 3.90 (s, 3H), 1.36 (s, 18H).

Example 8

Preparation of 3,5-di-tert.-Butyl-4'-hydroxybenzophenone 14.70 g (0.045 mole) of 3,5-di-tert.-butyl-4'-methoxybenzophenone are dissolved under an argon atmosphere in 200 ml of hydrobromic acid (33% solution in glacial acetic acid). 2.30 g (0.004 mole) of hexadecyltributylphosphonium bromide and 100 ml of hydrobromic acid (48% solution in water) are added and the solution is heated for 2 hours under reflux. A further 50 ml of hydrobromic acid (33% solution in glacial acetic acid) and 25 ml of hydrobromic acid (48% solution in water) are added. The solution is stirred for a further 2 hours under reflux.

After cooling the reaction mixture 300 ml of iced water are carefully added thereto. The mixture is extracted three times with diethyl ether. The combined organic phases are washed with saturated NaCl solution and dried over magnesium sulfate. The solvent is removed in vacuo. The crude product is recrystallised in a mixture of 200 ml of n-hexane and 0.30 ml of chloroform. A pale brown residue is obtained. The mother liquor is concentrated by evaporation-and the remaining residue is recrystallised again in a mixture of 80 ml of n-hexane and 5 ml of chloroform. The purified product fractions are combined. 7.50 g (53%) of product are obtained in the form of pale brown solid.

$^1$H-NMR (400 MHz, CDCl$_3$) δ=7.79 (d, 2H), 7.63 (s, 1H), 7.59 (s, 2H), 6.93 (d, 2H), 6.46 (s, 1H), 1.34 (s, 18H).

Example 9

Preparation of Polycarbonate with Branched Terminal Groups 8.56 g (0.038 mole) of 2,2-bis-(4-hydroxyphenyl)-propane and 3.30 g of NaOH (220 mole % referred to bisphenol component) are dissolved in 135 ml of water at room temperature under a nitrogen atmosphere in a round-bottomed flask. 0.86 g (2.3 mmoles) of 3,5-diphenyloxy-4'-hydroxybenzophenone (see Example 4) dissolved in 135 ml of dichloromethane are added to this mixture. The mixture is stirred for 5 minutes. 7.37 g (200 mole %, referred to bisphenol component) of phosgene are fed in at room temperature (25° C.) while stirring vigorously. The pH value is maintained in the range 12.5–13 by subsequent addition of 40% NaOH solution. After all the phosgene has been fed in the apparatus is flushed for 5 minutes with nitrogen. 0.042 g (1 mole %) of N-ethylpiperidine dissolved in 5 ml of dichloromethane is added to the reaction mixture. The mixture is stirred for 45 minutes. Following this the mixture is diluted with dichloromethane and the organic phase is separated. After extracting the organic phase with an equal volume of 10% hydrochloric acid, the organic phase is separated and washed 5 times with water until it is free of electrolyte. The polymer dissolved in the organic phase is precipitated in methanol and dried in, vacuo.

Yield:9.0 g (before precipitation)
$M_n$=8833 g/mole
$M_W$=19059 g/mole
D=2.16
$T_g$=142° C.

Example 10

Comparison Example

The preparation was carried out according to the procedure described in Example 9. As a departure therefrom, 6 mole % (referred to bisphenol component) of tert.-butylphenol is used in place of diphenyloxy-4'-hydroxybenzophenone as chain terminator.

Mn=10238
$M_W$=19431
D=1.90
$T_g$=148° C.

Example 11

Preparation of a Co-Polycarbonate with Branched Terminal Group, by the Melt Transesterification Process 31.96 g (0.14 mole) of bisphenol A, 11.16 g (0.06 mole) of dihydroxybiphenyl, 47.77 g (0.223 mole) of diphenyl carbonate, 0.76 g (0.002 mole) of 3,5-diphenyloxy-4'-hydroxy-benzophenone (see Example 6) and 0.0691 g ($8\times10^4$ mole % of a 5% phenolic solution) of tetraphenylphosphonium phenolate are weighed out into a 500 ml three-necked flask equipped with stirrer, internal thermometer and Vigreux column (30 cm, mirror coated) with bridge. The apparatus is freed from atmospheric oxygen by applying a vacuum and flushing with nitrogen (three times) and the mixture is melted at 150° C. and 100 mbar. The temperature is raised to 190° C. and the phenol formed is distilled off over 30 minutes. The temperature is now raised to 235° C. and the phenol formed is distilled off over 10 minutes. The vacuum is then adjusted to 60 mbar within 10 minutes and at the same time the temperature is adjusted to 300° C. After a further 10 minutes the vacuum is reduced to 0.5 mbar and the mixture is stirred for a further 30 minutes. A transparent polymer is obtained with a relative viscosity of 1.264.

Example 12

Comparison Example to Example 11

31.96 g (0.14 mole) of bisphenol A, 11.16 g (0.06 mole) of dihydroxybiphenyl, 45.84 g (0.214 mole) of diphenyl carbonate and 0.0691 g ($8\times10^{-4}$ mole % of a 5% phenolic solution) of tetraphenylphosphonium phenolate are weighed out into a 500 ml three-necked flask equipped with stirrer, internal thermometer and Vigreux column (30 cm, mirror coated) with bridge. The apparatus is freed from atmospheric oxygen by applying a vacuum and flushing with nitrogen (three times) and the mixture is melted at 150° C. and 100 mbar. The temperature is raised to 190° C. and the phenol formed is distilled off over 30 minutes. The temperature is now raised to 235° C. and the phenol formed is distilled off over 10 minutes. The vacuum is then adjusted to 60 mbar within 10 minutes and at the same time the temperature is adjusted to 300° C. After a further 10 minutes the vacuum is reduced to 0.5 mbar and the mixture is stirred for a further 30 minutes. A transparent polymer is obtained with a relative viscosity of 1.275.

Polycarbonates were produced similarly to Example 9 using the chain terminators 3,5-bis-7(3,5-di-tert.-butylphenyloxy)-4'-hydroxybenzophenone and 3,5-di-tert.-butyl-4'-hydroxybenzophenone (a precipitation of the polymer in methanol was omitted). These modified polycarbonates have a lower zero shear viscosity than polycarbonates of corresponding molecular weight that carry tert.-butylphenol as terminal group.

| Ex. No. | Terminal Group Used: | Zero Viscosity (Pa · s) (at 270° C.) | Molecular Wt. (g/mole) | Glass Transn. Temp. (° C.) |
|---|---|---|---|---|
| 9 | 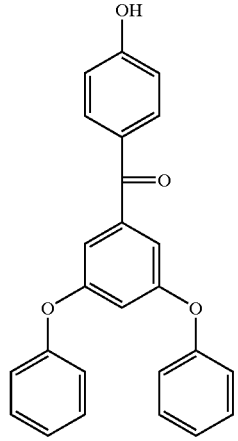 | 200 | $M_w$ = 19059<br>$M_n$ = 8833 | 142 |

-continued

| Ex. No. | Terminal Group Used: | Zero Viscosity (Pa · s) (at 270° C.) | Molecular Wt. (g/mole) | Glass Transn. Temp. (° C.) |
|---|---|---|---|---|
| 10 | OH-C6H4-C(CH3)3 | 300 | $M_w$ = 19431<br>$M_n$ = 10238 | 148 |
| 11 | OH-C6H4-CO-C6H3(OPh)2 | 420 | $M_w$ = 21229<br>$M_n$ = 9547 | 150.5 |
| 12 | OH-C6H5 | 500 | $M_w$ = 22528<br>$M_n$ = 10602 | 151 |

It is clear from the above table that the polycarbonates according to the invention, compared to polycarbonates with conventional terminal groups such as tert.-butylphenol or phenol and of approximately the same molecular weight, surprisingly have a reduced zero shear viscosity. This applies both to polycarbonates that have been produced in the phase interface process as well as polycarbonates that have been produced in the melt transesterification process.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for making a resin selected from the group consisting of polycarbonate, polyester carbonate and polyester comprising reacting at least one compound conforming to formula (1)

wherein
Ar$_1$ and Ar$_2$ independently denote an optionally substituted mononuclear or polynuclear aromatic moiety; X and Y independently denote a single bond or a divalent radical, W denotes an optionally substituted mononuclear or polynuclear aromatic moiety or an aliphatic or cycloaliphatic radical, and n is 1 to 5.

2. The process of claim 1 wherein the divalent radical is selected from the group consisting of —O— and —CO—.

3. A compound conforming to formula (2)

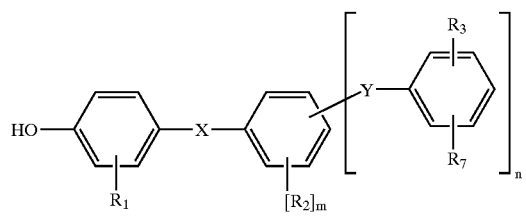

wherein
$R_1$ and $R_2$ independently denote H, linear or branched $C_1$–$C_{18}$-alkyl, I or Br, X and Y independently denote a single bond or a divalent radical, $R_3$ and $R_7$ independently denote H, linear or branched $C_1$–$C_{18}$-alkyl, cyclic $C_5$–$C_{18}$-alkyl, phenyl, phenyloxy, phenylcarboxy, benzyl, benzyloxy, naphthyl, naphthyloxy or naphthylcarboxy radicals,
m 0 to 3, and n denotes 2 to 5, wherein the total of m and n being $\leq 5$.

4. The compound of claim 3 wherein the divalent radical is selected: from the group consisting of —O— and —CO—.

5. A compound conforming to formula (3)

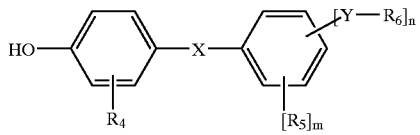

(3)

wherein X and Y independently of one another denote a single bond or a divalent radical, $R_4$ and $R_5$ independently of one another denote H, linear or branched $C_1$–$C_{18}$-alkyl, Cl or Br, and $R_6$ denotes linear or branched $C_1$–$C_{18}$-alkyl, cyclic $C_5$–$C_{18}$-alkyl, m is 0 to 3, and n is 2 to 5 and the sum of m and n being $\leq 5$.

6. The compound of claim 5 wherein the divalent radical is a member selected from the group consisting of —O— and —CO—.

7. A resin selected from the group consisting of polycarbonates, polyesters and polyester carbonates, the molecular structure of which includes units conforming to formula (4)

$$\text{—O—Ar}_1\text{—X—Ar}_2\text{—[Y—W]}_n \qquad (4)$$

wherein $Ar_1$ and $Ar_2$ independently denote an optionally substituted mononuclear or polynuclear aromatic moiety, X and Y independently denote a single bond or a divalent radical, W is an optionally substituted mononuclear or polynuclear aromatic parent group or an aliphatic or cycloaliphatic radical, and n is 1 to 5.

8. The resin of claim 7 wherein divalent radical is a member selected from the group consisting of —O— and —CO—.

9. A molded article comprising the resin of claim 7.

10. The molded article of claim 9 wherein resin is polycarbonate.

* * * * *